United States Patent [19]

Neti

[11] Patent Number: 5,633,170
[45] Date of Patent: May 27, 1997

[54] METHOD AND APPARATUS FOR NITROGEN OXIDE ANALYSIS

[76] Inventor: Radhakrishna M. Neti, 18561 Flora Dr., Yorba Linda, Calif. 92686

[21] Appl. No.: 403,494

[22] Filed: Mar. 14, 1995

[51] Int. Cl.[6] ........................................ G01N 21/76
[52] U.S. Cl. .................. 436/116; 436/115; 436/117; 436/118; 436/172; 423/239.1; 423/402; 423/405; 502/185
[58] Field of Search .................. 436/115, 116, 436/117, 118, 172; 423/239.1, 402, 405; 502/185

[56] References Cited

U.S. PATENT DOCUMENTS

| | | | |
|---|---|---|---|
| Re. 28,376 | 3/1975 | Warnick et al. | 436/116 |
| 3,652,227 | 3/1972 | Harman III | 23/232 R |
| 3,692,485 | 9/1972 | Neti et al. | 436/116 |
| 3,718,429 | 2/1973 | Williamson, Jr. | 436/118 |
| 3,746,513 | 7/1973 | Warnick et al. | 436/116 |
| 3,840,342 | 10/1974 | Neti et al. | 436/117 |
| 3,870,468 | 3/1975 | Neti | 23/232 R |
| 3,877,875 | 4/1975 | Jones et al. | 23/230 PC |
| 3,881,869 | 5/1975 | Neti et al. | 23/232 E |
| 3,934,991 | 1/1976 | Frain et al. | 55/316 |
| 3,963,923 | 6/1976 | Zolner | 250/361 C |
| 3,967,933 | 7/1976 | Etess et al. | 23/232 R |
| 3,973,914 | 8/1976 | Van Heusden | 23/254 E |
| 3,977,831 | 8/1976 | Fletcher et al. | 23/232 E |
| 3,984,688 | 10/1976 | Von Bargen et al. | 250/361 C |
| 4,063,895 | 12/1977 | Neti et al. | 23/232 R |
| 4,077,774 | 3/1978 | Neti et al. | 23/232 R |
| 4,081,247 | 3/1978 | Neti et al. | 23/232 E |
| 4,118,193 | 10/1978 | Neti et al. | 422/94 |
| 4,272,248 | 6/1981 | Neti | 23/232 R |
| 4,325,912 | 4/1982 | Sawa et al. | 422/95 |

OTHER PUBLICATIONS

Stuhl F. et al. (An Optical Detection Method for No in the Rage of $10^{-2}$ to $10^3$ ppm by the Chemiluminescent Reaction of NO w/$O_3$). Scientific Research Staff Technical Report (Ford) SR70–42 Oct. 12, 1973, pp. 1–21.

*Primary Examiner*—Jill Warden
*Assistant Examiner*—Sharidan Carrillo
*Attorney, Agent, or Firm*—John E. Vanderburgh

[57] ABSTRACT

A method and apparatus for the chemiluminescent determination of NO/$NO_x$ in a sample gas is disclosed in which the $NO_x$ portion of the gas stream is catalytically converted in a preconditioned vitreous carbon bed at a relatively low temperature effective to catalytically convert $NO_x$ to NO and below 200° C. The vitreous carbon is preconditioned by heating at a temperature of between 300° C. and about 500° C. for a sufficient period of time, on the order of two to five hours. The apparatus consists of a converter containing the preconditioned vitreous carbon in communication with a reaction cell consisting of a hollow cylindrical housing having an open end closed by an optical filter. A suitable photodetecter is disposed to detect light emitted through the optical filter. A chemiluminescent reaction between ozone and NO in the sample stream occurs in a reaction chamber defined by the interior of the housing. A reflector element may be disposed in the reaction chamber. The converter and the housing are preferably formed of low cost, easily worked materials, such as stainless steel or aluminum.

4 Claims, 2 Drawing Sheets

METHOD AND APPARATUS FOR NITROGEN OXIDE ANALYSIS

FIELD OF THE INVENTION

This invention relates to a method and apparatus for the analysis of gaseous nitrogen oxide and more particularly to improved method and apparatus for analysis of gaseous nitrogen oxide employing chemiluminescence.

BACKGROUND OF THE INVENTION

The analysis of gaseous samples for various air pollutants particularly NO and $NO_x$, has become increasingly important in recent years. One analytical technique which has proved particularly useful is the chemiluminescent reaction between NO and ozone. The quantity of light given off by the reaction is directly related to the quantity of NO in the sample being tested. $NO_x$ must first be converted to NO in a suitable converter for the subsequent chemiluminescent reaction with ozone. The conversion of $NO_x$ to NO is carried out in the presence of a suitable catalyst, such as platinum or activated carbon, at an elevated temperature, normally between 300° C. and 500° C.

The applications for chemiluminescent reactions in the detection of pollutants in gaseous samples was substantially enhanced by the introduction of an atmospheric pressure operated detector as described in U.S. Pat. No. 3,652,227, Neti et al. The design of the apparatus described therein, which forms the basis for many commercially available atmospheric pressure detectors, consists of a pair of nozzles bringing in two directed gas streams to form a point source in an extremely small reaction chamber having a volume on the order of a few cc. A sensitive photo-multiplier tube detector is closely coupled to the reaction chamber. The light emitted due to the reaction between ozone and a reactant gas is electronically measured by the photo-multiplier tube and the associated electronics. As mentioned above in order to measure the $NO_x$ concentration in a sample, the $NO_x$ must be converted to NO prior to its reaction with the ozone in the reaction chamber. This was accomplished by passing the sample gas containing $NO_x$ through a converter having a bed of vitreous carbon maintained at a temperature of between 300° C. to 500° C., see Neti et al. U.S. Pat. No. 4,081,247. In view of the relatively high temperatures at which the $NO_x$ is converted to NO and the resultant high reaction temperatures, the converter housing and the reaction cell must be formed of a material that is non-reactive with the sample gases at the reaction temperatures. The converter housing is conventionally formed from quartz tubing and the reaction chambers for atmospheric pressure chemiluminescent detectors are normally machined from teflon. In order to achieve maximum signal strength and speed of response, the internal volume of the reaction chamber should be held to close tolerances and to a minimum volume. In addition the sample gas stream and the ozone are brought together at a precise angle in order to form a point source.

Instruments built to these specifications are highly satisfactory for their purpose but the expense of manufacturing such instruments makes them unaffordable for low cost, high volume applications such as automobile emission testing. Accordingly it would be highly desirable to provide a low cost chemiluminescent detector operable at atmospheric pressure which has the sensitivity and response speed of high quality, high cost chemiluminescent detectors presently available.

SUMMARY OF THE INVENTION

The present invention provides a method and apparatus for the chemiluminescent determination of $NO/NO_x$ in a sample gas. The quantity of light emitted is directly related to the quantity of NO present in the sample stream. As is well understood, the $NO_x$ portion of the sample stream is catalytically converted to NO prior to entering the reaction chamber. The light output is detected by a suitable optical device such as a photo-multiplier tube or solid state silicon diodes and the signal produced by the optical device is processed in a conventional manner for direct readout and/or recording of the NO and/or the $NO_x$ concentration in the sample stream.

In accordance with the method of the present invention, the $NO_x$ portion of the gas stream is catalytically converted in a vitreous carbon bed maintained at temperature between that effective to catalytically convert $NO_x$ to NO but below about 250° C. to avoid reaction with the converter housing, the reaction cell and other components of the apparatus which may contacted by the hot nitrogen containing gas. The vitreous carbon is preconditioned by heating it at a temperature of between 300° C. and about 500° C. for a sufficient period of time, on the order of two to five hours, to precondition the vitreous carbon for catalytic conversion of the $NO_x$ at a substantially lower temperature than is conventional in the prior art.

The apparatus of the present invention comprises a converter consisting of a bed of preconditioned vitreous carbon in a suitable container. The container includes inlet means communicating with a source of the sample gas and outlet means for leading the sample gas out of the housing after contact with the vitreous carbon. A reaction cell comprises a tubular housing open at one end and having a pair of discharge tubes extending into the interior of the cell. One of the tubes is in communication with the outlet from the converter and the other tube is in communication with a source of ozone. The tubes are arranged to discharge their respective streams adjacent each other to mix the sample gas and ozone to cause the resultant chemiluminescent reaction. The open end of the cell is sealed by an optical filter through which selected frequencies of light generated by the chemiluminescent reaction passes. An optical measuring device is disposed adjacent the optical filter for detecting the light output and producing a signal in response to the detected light. The signal is led to a suitable processor for readout and/or storage.

In accordance with invention, the preconditioned vitreous carbon permits operation at substantially lower temperatures than prior art processes utilizing catalytic converters, including vitreous carbon converters, to convert $NO_x$ to NO. Operating at the lower temperatures permits use of materials of construction far less expensive than for conventional systems. For example materials such as stainless steel and aluminum, which normally react with nitrogen containing compounds at the normal operating temperatures for chemiluminescent systems, can be readily used in the apparatus of the present invention without interference caused by reaction between the metal and the nitrogen containing compounds. Furthermore, it has been unexpectedly found that the volume of the reaction chamber is not critical and good results are achieved utilizing a simple cylindrical housing at atmospheric pressure to carry out the chemiluminescent reaction. In addition the use of expensive thermal electric cooling systems to cool the photo-multiplier tube are eliminated. In place of the photo-multiplier tubes, solid state detectors can be utilized to detect the light output and in accordance with the invention multiple solid state detectors can be positioned about the light source to obtain the desired sensitivity at far less expense.

These and other features and advantages of the invention will become apparent from the following detailed description taken in conjunction with the drawings.

DETAILED DESCRIPTION OF THE INVENTION

Figure 1:
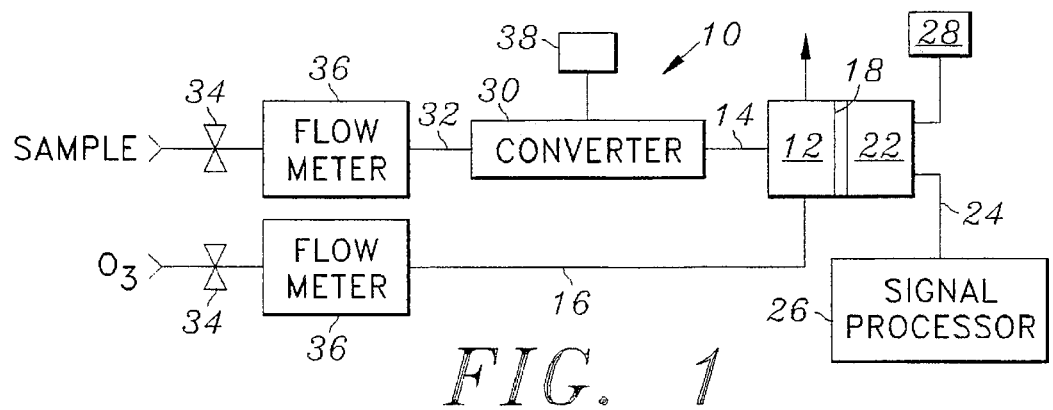
FIG. 1 is a schematic flow diagram of the apparatus of the present invention.

Referring to FIG. 1, the chemiluminescent analyzer, illustrated generally as 10, includes a hollow housing 12 which is open at one end and which is provided with an inlet line 14 for the introduction of a stream of sample gas to be tested and an inlet line 16 for introduction of ozone to the interior of the housing. The open end of the housing 12 is closed by an optical filter 18 which cooperates with the housing 12 to define a reaction chamber 20 which comprises a major portion of the interior of the housing. An optical detector 22, such as a photo-multiplier tube or one or more silicon solid state detectors are positioned in light detecting relationship adjacent the optical filter 18. The signal output from the optical detector 22 is carried through a line 24 to a signal processor 26 which includes suitable amplifying means and readout and recording means. A power supply 28 provides power for the optical detector 22.

The sample stream line 14 communicates with a catalytic converter 30 for converting $NO_x$ in the sample stream to NO. In accordance with the invention, the converter 30 contains preconditioned vitreous carbon prepared in accordance with the invention as will be explained below. The converter 30 communicates with a source of the sample stream by means of a line 32 and a valve 34 and flowmeter 36 are provided for controlling the flow to the converter. The ozone inlet line 16 communicates with a source of ozone, such as an ozone generator of conventional design, and a valve 34 and flow meter 36 are provided for controlling the flow rate of ozone to the reaction chamber 20.

The converter 30 has heating means 38 disposed adjacent thereto which is connected to an appropriate source (not shown) e.g. electricity, hot air, steam, to heat the converter 30 and the preconditioned vitreous carbon contained therein to a temperature between a catalytically effective temperature and less than about 200° C. The selection of the converter temperature is dependent upon the flow rate of the gas sample stream through the converter 30. Good results have been achieved by maintaining the vitreous carbon bed in the converter 30 at a temperature of about 120° C. with a sample gas flow rate of 200 cc/min. The conversion efficiencies achieved under these conditions are in excess of 93% over the minimum required by the Environmental Protection Agency even without a preheater for the sample stream.

In accordance with the method of the invention the vitreous carbon catalyst is preconditioned by heating the vitreous carbon in an oven for at least two hours at a temperature in excess of 300° C. Good results have been achieved when the vitreous carbon is preconditioned at a temperature of 400° C. for two hours. Following preconditioning, the vitreous carbon exhibits highly efficient catalytic activity at substantially lower conversion temperatures. The lower conversion temperature allows use of less expensive, more easily formed materials, such as stainless steel or aluminum, for the converter 30. These materials, if employed in a conventional detector at conventional conversion temperatures, are normally reactive and produce reaction products which can interfere with test results.

If desired the efficiency of the catalyst conversion can be improved by preheating the sample gas stream. This can be readily accomplished by passing the gas stream through a tubular coil wrapped around the converter 30 housing to heat the gas stream to approximately the converter temperature and then passing the heated gas stream back through the converter 30. The design and operation of such a preheating system is well known in the art and does not form a part of the present invention.

Figure 2:
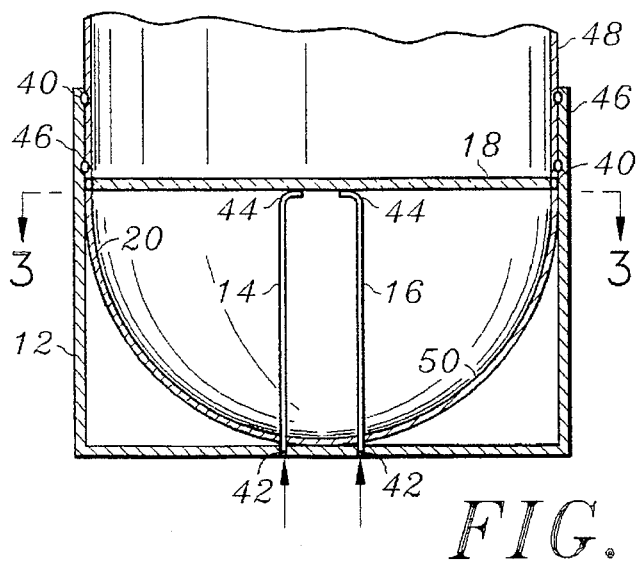
FIG. 2 is a side sectional view partially broken away for compactness of illustration of the reaction chamber of the present invention.
Figure 3:
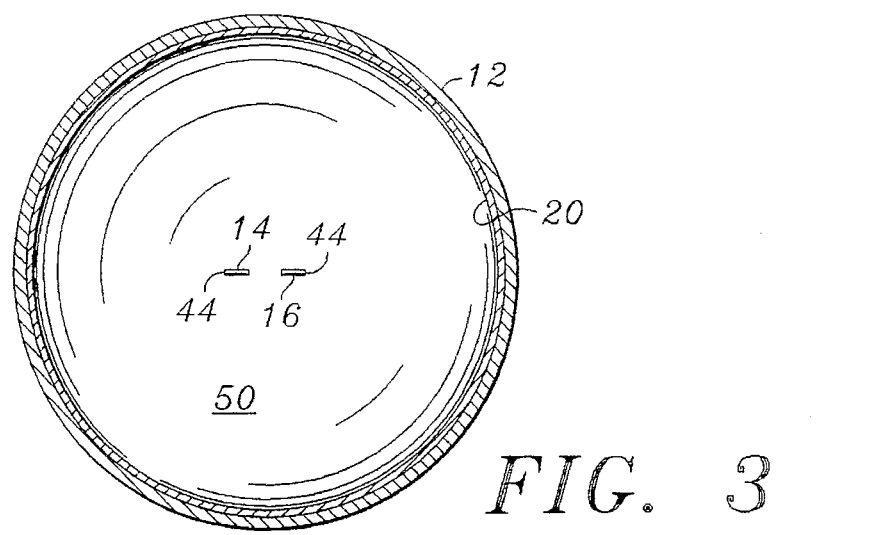
FIG. 3 is a top sectional view of the reaction chamber of FIG. 2 as viewed along line 3—3 of FIG. 2.

Referring to FIGS. 2 and 3, the reaction chamber 20 designed in accordance with the present invention includes an open ended cylindrical housing 12 closed at the open end by an optical filter 18 which cooperates with the walls of the cylindrical housing 12 to define the reaction chamber 20. The volume of the reaction chamber 20 comprises a major portion of the interior of the housing 12. In one embodiment of the invention the reaction chamber 20 had an internal diameter of 1.5 inches and a depth of 0.7 inch. The optical filter 18 is provided with a peripheral 0-ring 40 which acts against the walls of the housing 12 to provide a gas tight seal between the optical filter 18 and the housing 12. In this fashion the optical filter 18 can be removed to obtain access to the interior of the reaction chamber 20 for cleaning and the like. Alternatively a suitable bonding material, for example an epoxy resin, may be used to form the seal between the housing 12 and the optical filter 18.

The closed end of the housing 12 is provided with a pair of openings 42 through which extend the sample stream inlet line 14 and the ozone inlet line 16. The inlet lines 14 and 16 terminate adjacent the filter element and the terminal end portions 44 of the lines are turned inwardly toward each other so that the discharge stream of sample gas is countercurrent to the discharge stream of the ozone to facilitate mixing and the reaction between the sample gas and ozone.

As illustrated, the walls of the housing 12 extend beyond the filter element to define an annular sleeve 46 in which is received the end portion of a light shield 48 in which is disposed the optical detecting device 22. As previously mentioned the optical detecting device 22 may consist of a photo-multiplier tube or one or more solid state devices.

In a preferred embodiment of the invention, a semihemispherical reflector 50 is disposed in the reaction chamber 20. The reflector element 50 is located below the terminal end portions 44 of the inlet lines 14 and 16 and serves to reflect and focus stray emitted light back out of the reaction chamber 20 through the filter element 18 to the optical detector 22. The ability to incorporate the reflector 50 in the reaction chamber 20 is a function of the relatively large volume of the reaction chamber 20 and it has been found that the reflector 50 increases the light collection by a photo-multiplier by about 40%. The increase in light output due to the reflective element makes possible the detection of low levels of NO, on the order of 3 ppm with full scale sensitivity, without resorting to the use of expensive thermal electric cooling devices to cool the photo-multiplier.

By operating at temperatures below about 250° C. it is possible to construct the housing 12 and converter 30 out of much less expensive materials, such as for example stainless steel or aluminum, without the danger of the reaction of the metal with ammonia or other nitrogen containing substances in the sample gas stream. In addition, at the lower operating temperature the entire system operates cleanly and requires less cleaning and maintenance than with a conventional NO/NO$_x$ chemiluminescent reaction system. This is advantageous both from the standpoint of maintenance down time and for retaining the calibration of the analyzer for extended periods.

EXAMPLE 1

By way of example a reaction chamber 20 constructed in accordance with FIGS. 2 and 3 consisted of an open ended cylindrical stainless steel housing 12 closed at its open end with a red filter element 18 which transmitted light at a wave length of 600 millimicrons or longer. The reaction chamber 20 had an internal diameter of about 1.5 inches and a depth of 0.7 inch. The filter element 18 was fitted with an O-ring 40 to provide a gas tight seal with the walls of the reaction chamber 20. The converter 30, also formed from stainless steel tubing, contained preconditioned vitreous carbon which had been conditioned by heating at 400° C. for two hours. The vitreous carbon in the converter 30 was maintained at a temperature of 120° C. during the operation of the analyzer. The sample gas stream was led directly into the converter 30 without preheating. The sample flow was maintained a rate of 200 cc/min and the ozone flow rate was about 100 cc/min. The gases were introduced to the reaction chamber 20 at atmospheric pressure. The instrument had a response time of less than 0.6 seconds and provided conversion efficiencies on the order of 99%.

EXAMPLE 2

Figure 4:
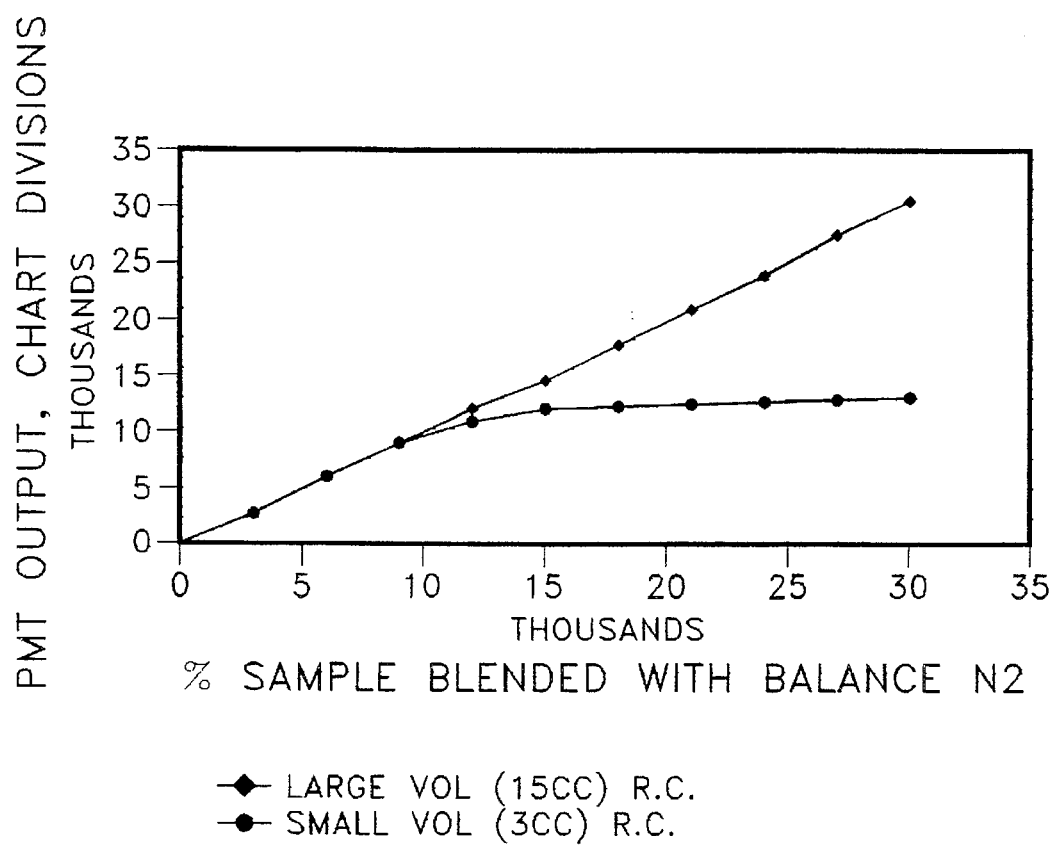
FIG. 4 is a plot of of meter output versus percent of test sample for a conventional FID and one constructed in accordance with the invention.

To demonstrate the advantages of the larger reaction chamber 20 designed in accordance with the invention, apparatus as described in Example 1 above utilizing the preconditioned carbon was used to analyze a sample containing 30,000 ppm of NO in N$_2$ which was diluted in N$_2$ in concentrations ranging from 10% to 100% of NO. One run was made using a reaction chamber having a volume of about 3 cc and a second run was made using the reaction chamber described above, having a volume of about 15 cc. Sample flow was maintained at 55 cc/min and ozone pressure was 5.5 psig. As described above the vitreous carbon was preconditioned at 400° C. and the stainless steel converter was held at a temperature of 120° C. during each run. The PMT output in parts per million was recorded and plotted against the parts per million of NO in the test gas (FIG. 4). The results are set forth in the table below.

TABLE A

| | Observed Conc./ppm Chamber Vol | |
|---|---|---|
| Conc. Sample/ppm | 3 cc | 15 cc |
| 0 | 0 | 0 |
| 3000 | 3000 | 2940 |
| 6000 | 5926 | 5760 |
| 9000 | 8519 | 8700 |
| 12000 | 11125 | 11640 |
| 15000 | 11938 | 14550 |
| 18000 | 12250 | 17550 |
| 21000 | 12313 | 20400 |
| 24000 | 12500 | 23400 |
| 27000 | 12500 | 26940 |
| 30000 | 12500 | 29640 |

EXAMPLE 3

To demonstrate the efficiency of the converter, 500 ppm of a test mixture consisting of about 480 ppm of NO and about 20 ppm of NO$_2$ was passed through the stainless steel converter 30 containing carbon that had been preconditioned at 400° C. as described above. After conversion the sample was analysed for NO content using the apparatus described in Example 1. Separate runs were made operating the converter 30 at temperatures ranging from 140° to 259°. the results are set forth in Table 2 below.

TABLE B

| | Conversion Efficiency; NO$_x$ to NO | |
|---|---|---|
| Temp. °C. | Ratio NO$_x$/NO, ppm | Efficiency |
| 259 | 1.030 | 99.0 |
| 188 | 1.037 | 99.7 |
| 161 | 1.030 | 99.0 |
| 140 | 1.017 | 97.7 |

While the invention has been described in connection with certain preferred embodiments thereof it will be understood by those skilled in the art that various arrangements and modifications will occur to those persons other than those described in detail in this specification, which arrangements and modifications lie within the spirit and scope of the invention. It is therefore to be understood that the invention is to be limited only the claims appended hereto.

Having described the invention, I claim:

1. In a method for the determination of the concentration of NO$_x$ in a gas stream by the catalytic conversion of NO$_x$ to NO, mixing the NO with ozone in a reaction chamber to cause a chemiluminescent reaction therebetween and determining the light output of said reaction as a measure of the concentration of the NO$_x$ in said sample, the invention comprising the steps of:

a. preconditioning a catalyst comprising vitreous carbon by heating said vitreous carbon to a temperature in excess of 300° C. for at least two hours;

b. forming a converter comprising a housing and a bed of said preconditioned vitreous carbon and heating said bed of vitreous carbon to a temperature effective to convert NO$_x$ to NO and less than 200° C.; and c. passing said gas stream through said converter to convert a major portion of the NO$_x$ concentration thereof to NO.

2. The method of claim 1 wherein said vitreous carbon bed is maintained at a temperature between about 120° C. and 200° C. while passing said gas stream therethrough.

3. The method of claim 2 wherein said gas stream is passed through said converter at flow rate of between 55 cc/min and 200 cc/min.

4. The method of claim 1 wherein said vitreous carbon bed is maintained at a temperature of 120° C. and said gas stream is brought into contact therewith at a flow rate of 200 cc/min.

* * * * *